United States Patent

Boebel et al.

[11] Patent Number: 5,312,433
[45] Date of Patent: May 17, 1994

[54] SURGICAL FORCEPS

[75] Inventors: Manfred Boebel, Oetisheim; Dieter Metsch, Kraichtal/Bahnbrücken, both of Fed. Rep. of Germany

[73] Assignee: Richard Wolf GmbH, Knittlingen, Fed. Rep. of Germany

[21] Appl. No.: 947,185

[22] Filed: Sep. 18, 1992

[30] Foreign Application Priority Data

Sep. 19, 1991 [DE] Fed. Rep. of Germany ....... 4131176

[51] Int. Cl.$^5$ .............................................. A61B 17/32
[52] U.S. Cl. ..................................... 606/205; 128/751
[58] Field of Search ............... 606/87, 174, 205–210, 606/51, 52; 128/750–755

[56] References Cited

U.S. PATENT DOCUMENTS

| H1,028 | 3/1992 | Falk et al. | 606/205 |
| 4,896,678 | 1/1990 | Ogawa | 128/751 |

FOREIGN PATENT DOCUMENTS

| 0351165 | 1/1990 | European Pat. Off. | 606/206 |
| 3601166 | 1/1987 | Fed. Rep. of Germany | 606/205 |
| 3741879 | 6/1988 | Fed. Rep. of Germany. | |
| 3709067 | 9/1988 | Fed. Rep. of Germany. | |
| 3739254 | 6/1989 | Fed. Rep. of Germany. | |
| 3819123 | 12/1989 | Fed. Rep. of Germany. | |
| 4115937 | 5/1992 | Fed. Rep. of Germany. | |

Primary Examiner—Stephen C. Pellegrino
Assistant Examiner—William W. Lewis
Attorney, Agent, or Firm—Panitch Schwarze Jacobs & Nadel

[57] ABSTRACT

Surgical forceps, for example for endoscopic use, having distal mouth parts which are actuated by means of proximal grip sections via a rod and are mounted displaceably in the tubular forceps housing. An overload safety device, which prevents further actuation on exceeding a certain actuation force by radially deflecting the rod or a section of it against spring action and positively engaging it with a fixed part of the forceps housing, is provided to protect the sensitive mouth parts.

5 Claims, 1 Drawing Sheet

SURGICAL FORCEPS

BACKGROUND OF THE INVENTION a) Field of the Invention

The invention relates to surgical forceps having distal mouth parts, at least one mouth part of which can be movably actuated against the other by means of a proximal handle, wherein the force exerted when actuating the handle can be transferred to the movable mouth part by means of an axially displaceable rod, and wherein overload protection is provided which is effective in the case of overload with danger of breakage and limits the closing force of the mouth parts to a preset value.

b) Description of the Prior Art

Surgical forceps of the type mentioned above having cutting, stamping or clamping and holding distal mouth parts must be protected against overload and danger of breakage, particularly since the force exerted by the handle on the distal mouth parts may be relatively large as a result of the existing leverage.

In a known design of forceps of this type, it is possible to achieve overload protection by means of safety devices which are introduced onto the handle, such as for example according to German Patentschrift 3 601 166 by a spring, which, according to a first exemplary embodiment, bridges the two-part forceps grip arranged to be pivotable under spring pretension and, according to a second exemplary embodiment, bridges the connecting and forcing rod connected to the pivotable forceps mouth part under spring pretension, and absorbs the further compressive force exerted on the two forceps grips when the breaking force is exceeded.

In both embodiments, only the movable grip section of the handle is deflected further on reaching a certain force and the mouth part no longer moves, but the force exerted on the mouth parts increases further in accordance with the spring characteristic. Furthermore, it is not possible for the operator to clearly perceive in which actuation position the actuation force exceeds the spring pretension, since this transition is fluid. Uncertainties may arise during handling because of this.

In German Offenlegungsschrift 3 709 067, a disengaging coupling is provided between the movable grip section and the connecting and forcing rod, wherein a coupling part mounted resiliently in a grip section engages and disengages in a recess in the rod if a certain force is exceeded. This transition is not fluid, it is abrupt, wherein the movable grip section is completely uncoupled by the rod. This design also conceals uncertainties in the handling.

It is the object of the invention to find overload protection for surgical forceps of the type mentioned which acts safely and makes it possible for the operator to work with sensitivity, wherein the moment of onset of overload should be detectable by the operator.

SUMMARY OF THE INVENTION

This object is achieved according to the invention in that on reaching the overload state, the rod or at least a section of the rod can be laterally deflected and can be brought into positive engagement blocking further actuation of the forceps handle by means of a fixed part of the forceps.

This makes it possible for both the rod and the movable mouth part as well as the handle to be stopped immediately from further movement on overload. This state can be detected directly and immediately by the operator and makes it possible to carry out much safer handling than before.

According to a preferred embodiment of the invention, the axially displaceable rod of the forceps is comprised of positively connected sections, at least one of which can be deflected radially against spring action on reaching the overload state and thus engages with the fixed part of the forceps. The spring force is adapted to the durability of the mouth parts and thus ensures optimum safety against breakage.

Advantageously, the rod is comprised of two sections guided axially with respect to one another by means of a cylindrical tube section and a part region of one of the rod sections passes through a longish peripheral recess of the cylindrical tube section with resilient deformation in the overload state and the upper surface engages positively with an inner surface of the forceps housing.

In another preferred embodiment, the two rod sections overlapping one another in the overlap region are provided with a reduced cross-section and several tooth flanks effecting radial deflection during axial displacement of the rod sections with respect to one another, wherein teeth introduced on the outer sides engage with the similarly toothed inner surface of the forceps housing during radial deflection.

Alternatively, the two ends of the rod sections are fixed in a resilient, cylindrical tube element having several longitudinal slots distributed uniformly on the periphery, which tube element experiences a resilient increase in diameter when the two rod sections are axially displaced with respect to one another, as a result of which the upper surface comes to rest against the inner surface of the forceps housing.

BRIEF DESCRIPTION OF THE DRAWINGS

The foregoing summary of the invention, as well as the following detailed description of the preferred embodiments, will be better understood when read in conjunction with the appended drawings. For the purposes of illustrating the invention, there are shown in the drawings embodiments which are presently preferred, it being understood, however, that the invention is not limited to the specific arrangements and instrumentalities disclosed.

DESCRIPTION OF THE PREFERRED EMBODIMENTS

Figure 1:
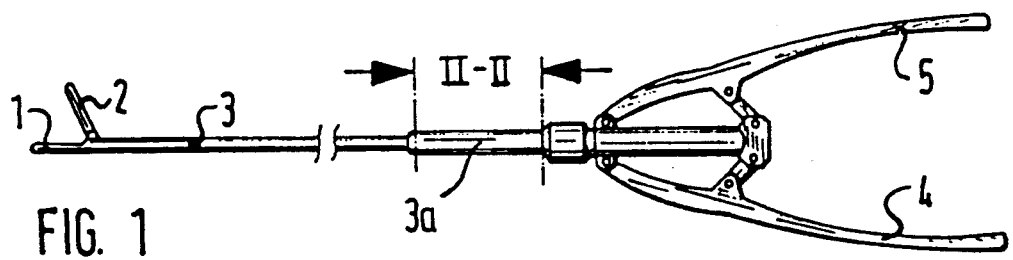
FIG. 1 shows a side view of the forceps on a reduced scale.

The forceps according to FIG. 1 may be designed as cutting, holding or clamping forceps. They consist essentially of mouth parts 1 and 2, of which the mouth part 2 is movable in the exemplary embodiment, and also of the shaft 3 as the forceps housing and the handle consisting of grips 4 and 5 to be actuated like scissors. Of these, the grip 5 is connected to the shaft section 3a of the housing and the grip 4 is mounted thereon as pivotable lever. The two-part rod 6, 7, which is linked by its section 7 at the movable mouth part 2 and moves the latter, is actuated by this grip 4.

The rod section 7 is provided with a moulding 8 which engages positively in a moulding 9, which is in turn connected to the rod section 6. The positive engagement of the two mouldings 8 and 9 in one another takes place by means of teeth 10. A tube sleeve 11 is provided in order to keep the two mouldings 8 and 9 together or to guide them together. This tube sleeve 11 has a longish peripheral recess 12 (shown by the curved dotted lines).

The two mouldings 8 and 9 kept together by means of the tube sleeve 11 in accordance with the representation, are axially displaced together with the rod sections 6 and 7 in the same direction and with the same path during normal actuation of the grip 4, so that the mouth part 2 is moved. If the movable mouth part 2 comes to rest against the fixed mouth part 1 or in some other way is prevented from further movement, so that destruction of the mouth parts or their mounting is threatened by the force acting at the grips 4 and 5, the flanks of the teeth 10 of the two mouldings 8 and 9 slide over one another, as a result of which the moulding 8 is deflected like a resilient spring radially outwards against the shaft section 3a.

The moulding 8 is provided on its outer side with a structure 13, for example in the form of threaded flanks or toothed flanks. The latter may engage in an appropriately shaped counter surface 14 on the inner side of the shaft section 3a, if the deflection as a result of overload is large enough. This produces positive engagement between rod section 7 with moulding 8 and the fixed shaft section 3a. This engagement blocks the further axial movement of the rod section 7 and hence also that of the rod section 6 in the actuation direction. Further actuation is blocked and hence damage to the sensitive mouth parts 1 and 2 is prevented. The parts automatically occupy their original position with diminishing actuation force.

Figure 2:
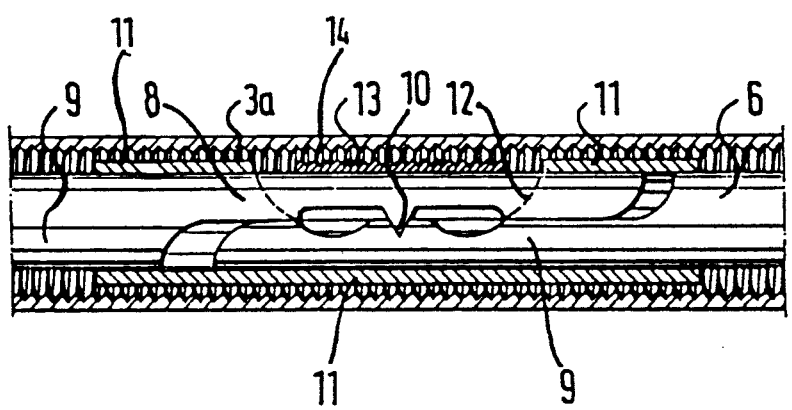
FIG. 2 shows a sectional representation along the line II—II on an enlarged scale.
Figure 3:
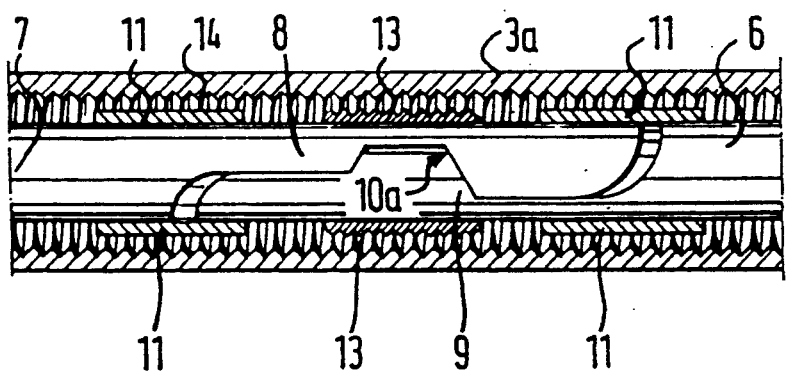
FIGS. 3 and 4 show sectional representations as for FIG. 2, but using other embodiments.

In contrast to the exemplary embodiment according to FIG. 2, in which only the moulding 8 can be resiliently deflected, in the example shown by FIG. 3 the mouldings 8 and 9, as components of the rod sections 6 and 7 and as a result of their shaping or reduction in cross-section, can be deflected like a resilient spring. The positive engagement of these two sections to one another need not necessarily take place by means of several tooth flanks 10 (as in FIG. 2), but may be formed by two cooperating flanks 10a. Both mouldings 8, 9 have tooth structures 13 on the outer sides, while the inner side of the shaft section 3a is also provided with a structure 14 over a greater length, that is roughened, toothed or provided with a thread. On overload, both mouldings 8 and 9 as components of the rod sections 6 and 7 slide radially apart on the flanks 10a and engage positively with the teeth 13 in the inner structure 14 of the shaft section 3a, so that further displacement of the rod and overloading of the mouth parts is thus prevented. This primary engagement offers even more security against further damaging actuation in the overload region. In order to fix the two rod sections 6 and 7 with respect to one another and to guide them axially, two spaced apart tube sleeves 11 are provided instead of a single tube sleeve with a cutout 12 (as in FIG. 12).

Figure 4:
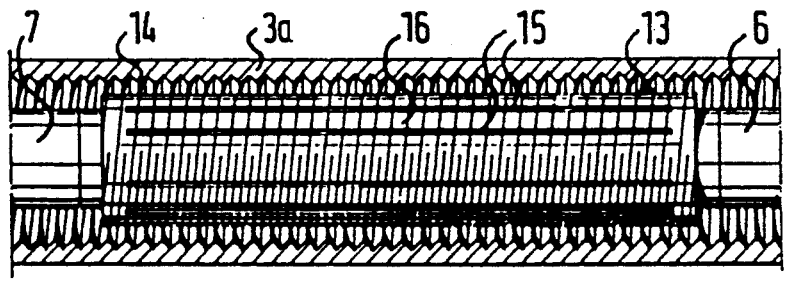

A further possible embodiment of the invention is shown in FIG. 4. The shaft section 3a of the housing is again provided with inner teeth 14, thread structure or scored structure. The two rod sections 6 and 7 are connected to one another by means of a tube element 16 having outer teeth 13 or the like and having several longitudinal slots 15 distributed uniformly over the periphery, which tube element experiences a resilient increase in diameter if the two rod sections are displaced with respect to one another under the destructive effect of force.

Deviating from the exemplary embodiments shown, both mouth parts 1, 2 could also be actuated using the connecting and forcing rod sections 6, 7. Furthermore, the rod mentioned may also be designed in one piece, wherein in the overload state, a region, for example the central or end region, of the rod is deflected resiliently and engages with a fixed part of the forceps.

The present invention may be embodied in other specific forms without departing from the spirit or essential attributes thereof and, accordingly, reference should be made to the appended claims rather than to the foregoing specification as indicating the scope of the invention.

We claim:

1. Surgical forceps comprising a hollow shaft, a forceps mouth having two mouth parts at the distal end of the shaft, at least one of the mouth parts being movably actuatable against the other by means of a handle at the proximal end of the shaft, an axially displaceable actuating rod riding in the hollow shaft, wherein the force exerted by actuating the handle is transferred to the movable mouth part by means of the axially displaceable rod, and overload protection means in a section of the shaft for limiting the closing force of the mouth parts to a preset value when an overload state occurs with danger of breaking the forceps mouth, wherein at least one section of the rod inside the shaft is connected to a first blocking element which upon reaching the overload state is laterally deflected by said one section toward a second blocking element on the inner wall of the shaft and brought into positive engagement with said second blocking element, thereby blocking further actuation of the handle.

2. Forceps according to claim 1, wherein the rod comprises positively connected sections, at least one of which has said first blocking element which is deflected radially upon reaching the overload state, thereby engaging the second blocking element.

3. Forceps according to claim 1, wherein the rod comprises two rod sections and a cylindrical sleeve section, the rod sections being guided axially with respect to one another by means of the cylindrical sleeve section and wherein a part of one of the rod sections passes through a peripheral recess in the cylindrical sleeve section in the overload state such that the first blocking element on the rod section engages positively with the second blocking element on the inner shaft wall.

4. Forceps according to claim 1, wherein the rod comprises two rod sections which overlap one another in an overlap region, the rod sections having reduced cross-section in the overlap region and said first blocking element comprising teeth formed on outer sides of the rod sections in the overlap region, and said second blocking element comprising a similarly toothed inner surface of the hollow shaft in the overlap region, such that radial deflection is effected during axial displacement of the rod sections with respect to one another, wherein the rod section teeth engage the similarly toothed inner surface of the shaft during the radial deflection.

5. Forceps according to claim 1, wherein the rod comprises two rod sections, each having ends which are fixed in a resilient, cylindrical tube element having several longitudinal slots distributed uniformly on a periphery of the tube element, and wherein a diameter of the tube element resiliently increases when the two rod sections are axially displaced with respect to one another, said first blocking element being provided on the outside of said tube elements such that when a diameter of the tube element increases said first blocking element engages the second blocking element means on the inner wall of the shaft.

* * * * *